(12) United States Patent
Nieva et al.

(10) Patent No.: US 8,693,003 B2
(45) Date of Patent: Apr. 8, 2014

(54) METHOD AND APPARATUS FOR AN INTERFEROMETRIC LOCALIZED SURFACE PLASMON RESONANCE (ILSPR) SENSOR

(76) Inventors: Patricia Marlen Nieva, Mississauga (CA); Ryan Cameron Denomme, Zurich (CA)

(*) Notice: Subject to any disclaimer, the term of this patent is extended or adjusted under 35 U.S.C. 154(b) by 315 days.

(21) Appl. No.: 13/091,805

(22) Filed: Apr. 21, 2011

(65) Prior Publication Data

US 2011/0261364 A1 Oct. 27, 2011

Related U.S. Application Data

(60) Provisional application No. 61/282,921, filed on Apr. 22, 2010.

(51) Int. Cl.
*G01B 9/02* (2006.01)
*G01J 3/45* (2006.01)

(52) U.S. Cl.
USPC .......................................................... 356/451

(58) Field of Classification Search
USPC ........................................ 356/445, 450–521
See application file for complete search history.

(56) References Cited

U.S. PATENT DOCUMENTS 7,817,278 B2* 10/2010 VanWiggeren ................ 356/445
2009/0040507 A1* 2/2009 VanWiggeren ................. 356/73

OTHER PUBLICATIONS

Hiep et al. (Hiep, Ha Minh et al., An Interference Localized Surface Plasmon Resonance Biosensor Based on the Photonic Structure of Au Nanoparticles and SiO2/Si Multilayers, ACS Nano, vol. 3, No. 2 (2009), pp. 446-452, available online Feb. 4, 2009 at www.acsnano.org).*
Endo et al. (Endo, Tatsuro et al., Multiple Label-Free Detection of Antigen-Antibody Reaction Using Localized Surface Plasmon Resonance-Based Core-Shell Structured Nanoparticle Layer Nanochip, Anal. Chem., vol. 78, No. 18 (Sep. 15, 2006), pp. 6465-6475) teaches a nanochip.*
Hiep et al. (Hiep, Ha Minh et al., Interference Localized Surface Plasmon Resonance Nanosensor Tailored for the Detection of Specific Biomolecular Interactions, Anal. Chem., vol. 82, No. 4 (Feb. 15, 2010), pp. 1221-1227, available online Jan. 14, 2010).*
Homola (Homola, Jiri, Surface Plasmon Resonance Sensors for Detection of Chemical and Biological Species, Chem. Rev., vol. 108, No. 2 (2008), pp. 462-493, available online Jan. 30, 2008).*
Homola et al. (Homola, Jiri et al., Surface Plasmon Resonance Biosensors, Optical Biosensors: Present and Future, Elsevier Science B.V. (2002), Chapter 7, pp. 207-251).*
Huang et al. (Huang, Chengjun et al., An on-chip localized surface plasmon resonance-based biosensor for label-free monitoring of antigen-antibody reaction, Microelectronic Engineering 86 (2009), pp. 2437-2441, available online May 18, 2009 at www.elsevier.com) teaches a microfluidic integrated LSPR-based biosensor.*

(Continued)

*Primary Examiner* — Michael A Lyons
(74) *Attorney, Agent, or Firm* — Borden Ladner Gervais LLP; Jeffrey W. Wong (57) ABSTRACT

The disclosure is directed at an interferometric localized surface plasmon resonance sensor (ILSPR) unit comprising an ILSPR sensor chip, the sensor chip including a localized surface plasmon resonance sensor (LSPR) layer; at least one light source for directing light through the ILSPR sensor chip at the LSPR layer; and a photodetector for sensing a level of light intensity after the light has struck the LSPR layer.

22 Claims, 9 Drawing Sheets

(56) References Cited

OTHER PUBLICATIONS

Kim et al. (Kim, Do-Kyun et al., Label-Free DNA Biosensor Based on Localized Surface Plasmon Resonance Coupled with Interferometry, Anal. Chem., vol. 79, No. 5 (Mar. 1, 2007), pp. 1855-1864, available online Jan. 30, 2007).*

Lecaruyer et al. (Lecaruyer, Pierre et al., Generalization of the Rouard method to an absorbing thin-film stack and application to surface plasmon resonance, Applied Optics, vol. 45, No. 33 (Nov. 20, 2006), pp. 8419-8423).*

Malinsky et al. (Malinsky, Michelle Duval et al., Chain Length Dependence and Sensing Capabilities of the Localized Surface Plasmon Resonance of Silver Nanoparticles Chemically Modified with Alkanethiol Self-Assembled Monolayers, J. Am. Chem. Soc., vol. 123, No. 7 (2001), pp. 1471-1482) teaches "standard transmission geometry" equipment set-up for.*

Malitson (Malitson, I. H., Interspecimen Comparison of the Refractive Index of Fused Silica, J. Opt. Soc. Am., vol. 55, No. 10 (Oct. 1965), pp. 1205-1209).*

Piliarik et al. (Piliarik, Marek et al., Surface Plasmon Resonance Biosensing, Methods in Molecular Biology: Biosensors and Biodetection, vol. 503, Humana Press (2009), Chapter 5, pp. 65-88).*

Kim D.K. et al., Label-Free DNA Biosensor Based on Localized Surface Plasmon Resonance Coupled with Interferometry, Analytical Chemistry, Mar. 1, 2007, vol. 79, No. 5, pp. 1855-1864.

Canadian Intellectual Property Office as International Searching Authority, International Search Report and Written Opinion for International patent application No. PCT/CA2011/000466, Aug. 23, 2011.

* cited by examiner

METHOD AND APPARATUS FOR AN INTERFEROMETRIC LOCALIZED SURFACE PLASMON RESONANCE (ILSPR) SENSOR

CROSS-REFERENCE TO RELATED APPLICATIONS

This application claims the benefit of U.S. Provisional Patent Application No. 61/282,921, filed Apr. 22, 2010, which is hereby incorporated by reference.

FIELD

The disclosure is directed to sensors and more specifically is directed at a method and apparatus for an interferometric localized surface plasmon resonance (ILSPR) sensor.

BACKGROUND

Rapid and definitive diagnosis of cardiac injury, including ischemia and infarct, is challenging. Patients frequently arrive at the emergency room with non-specific symptoms, which have a broad differential diagnosis. In most cases of chest pain, cardiac etiology must be ruled out. This necessitates a large number of lengthy and costly tests, and extended stays in overcrowded emergency rooms (ERs). In a 2006 study, Christenson and colleagues analyzed a group of 1819 patients at the ER with symptoms typical of acute cardiac injury. Of these, only 22% were experiencing cardiac injury. However, of the patients without an adverse cardiac event, up to 71% were either admitted to hospital or spent more than 3 hours in the ER. This represents a significant drain on the limited resources of the healthcare system, and exacerbates the nationwide problem of overcrowding and long wait times in the nation's ERs. More importantly, over 5% of patients who were undergoing a significant cardiac event were misdiagnosed and discharged without intervention. Pope and colleagues showed that missed diagnoses of cardiac events leads to increased risk of 30-day morbidity and mortality. They reported a risk ratio of 1.9 for mortality of patients who were not hospitalized versus patients who were hospitalized following acute cardiac injury.

Therefore, there is provided a method and apparatus for a novel interferometric localized surface plasmon resonance (ILSPR) sensor which overcomes some disadvantages in the prior art.

DESCRIPTION OF THE DRAWINGS

Embodiments of the present invention will now be described, by way of example only, with reference to the attached Figures, wherein.

DETAILED DESCRIPTION

The disclosure is directed at an interferometric localized surface plasmon resonance (ILSPR) sensor unit for use in detecting the presence of a protein or a chemical within a test substance, or complex solution. In one of the protein detection embodiments, the sensor unit may provide earlier detection of diseases or biohazards for patients with respect to current detection systems. The sensor unit may be portable or may be a stand-alone unit.

In one embodiment, the detection by the sensor is performed by determining if the spectral response (either in reflectance or in transmission) of the system is changed after the introduction of the test substance. A change in the reflectance (or transmittance) value in relation to a baseline value would indicate the likely presence of a protein or chemical of interest while a lack of chance in the reflectance (or transmittance) value in relation to a baseline value would indicate the likely absence of a protein or chemical of interest. The comparison may be based on the reflectance (or transmittance) value being at least a percentage of the baseline value or the reflectance or transmittance) value being a certain amount less than or more than the baseline value.

Figure 1:
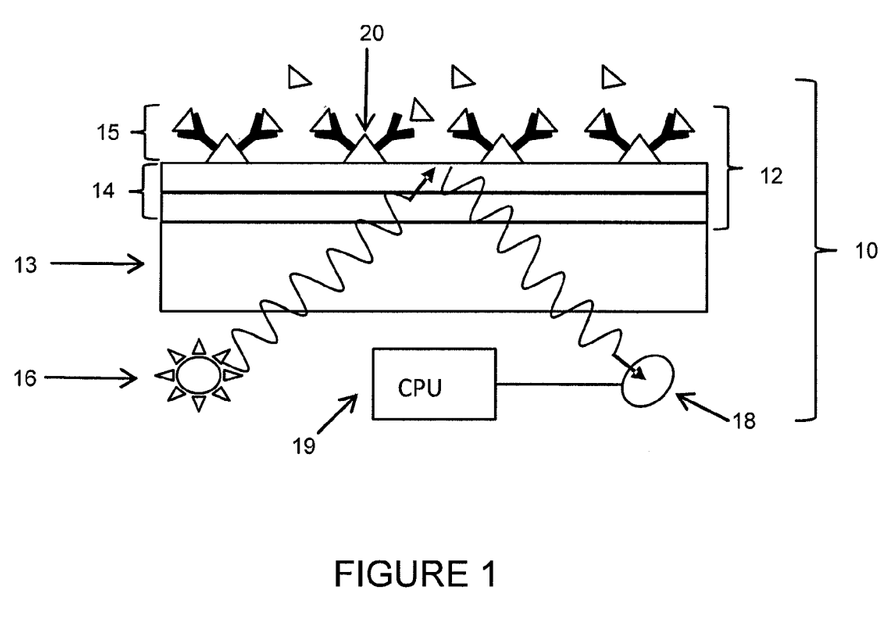
FIG. 1 is a schematic diagram of an interferometric sensor unit for use in a reflection mode.

Turning to FIG. 1, a schematic diagram of an ILSPR sensor, or sensing, unit is shown. In this embodiment, the sensor unit 10 may be used for a label-free hand held protein sensing unit which may find benefit in applications such as, but not limited to, field analysis of Heat Shock Protein 70 (HSP 70) in animals for assessing the health of ecological systems or real time monitoring of various biomarkers of myocardial infarction in humans for early prediction of heart attacks.

In the current embodiment, the sensor unit 10 includes an ILSPR sensor chip 12 which comprises an interferometric sensing, or interference, layer 14, such as a reflectometric interference spectroscopy (RIfS) layer, and a localized surface plasmon resonance (LSPR) layer 15 which may include a buffer, or dielectric medium, located atop the RIfS layer 14. The sensor chip 12 may also include a substrate layer (such as glass) 13 where the interferometric sensing layer may be deposited. The RIfS layers may function as a narrowband filter so that light within a narrow range of wavelengths may be transmitted through the layer 14. In one embodiment, the RIfS layer 14 comprises a set of individual layers such as a high refractive index material layer and a low refractive index material layer with the high refractive index material layer stacked atop the low refractive index material layer or vice versa. In the embodiment of FIGS. 4a to 4e, the high refractive index material is $Ta_2O_5$ and the low refractive index material is $SiO_2$. In an alternative embodiment, the RIfS layer 14 may comprise any number of layers of different refractive index material stacked atop each other.

In the embodiment of FIG. 1, the sensor unit 10 is used in a reflection mode. In another embodiment, the ILSPR sensor chip 12 may be used in a transmission mode rather than a reflection mode as will be shown and described with respect to FIG. 8.

The sensing unit 10 further comprises a light source 16 located on one side of the sensor chip 12. The light source may be a light emitting diode (LED) or may be a white light source depending on the application of the sensor. Alternatively, a plurality of light sources including an LED light source and a white light source may be placed on the one side of the sensor chip 12. Adjacent to the light source 16 is a photodetector 18 which may be used to detect changes in the refractive index as will be described below.

The ILSPR sensor chip 12 includes a nanoparticle array 15 which is preferably fabricated atop the RIfS sensor layer 14. One example of how this may be performed is described below. This nanoparticle array 15 may be seen as the LSPR sensor layer. The nanoparticle array 15 is preferably submerged within a dielectric medium or buffer. The dielectric medium or buffer is a solution that is used to transport biological entities such as the proteins. It is similar to water but has a well controlled pH and additional salts added. An example of a buffer is Phosphate Buffered Saline (PBS) which may contain salts such as sodium chloride and potassium chloride.

In this reflectance or reflection mode embodiment, the nanoparticle array 15 is located on a side of the ILSPR sensor chip 12 opposite the light source 16 so that the light source may direct light through the RIfS layer 14 towards the nanoparticle array 15 and then the photodetector 18 may then detect the reflected light rays. In the preferred embodiment, the light source and detector are aligned, but there are no strict requirements on the positioning. As long as the light is passing through or reflecting off of the nanoparticle surface and going to the detector, the sensing unit may operate correctly.

The photodetector which may also be a photodiode or a charge-coupled device (CCD) 18 is in communication with a central processing unit (CPU) 19 or may be located on a signal processing chip so that the reflected light rays detected by the photodetector may be processed to determine if a specific protein or chemical of interest is located in a test substance.

In one embodiment, each sensor, or sensing unit, is dedicated to the detection of a specific protein and therefore, individual nanoparticles within the nanoparticle array 20 may be coated with a specific self-assembled monolayer (SAM) of alkanethiol based molecules. Other materials, such as various polymers, are also contemplated. The SAM-coated nanoparticle may be seen as a functionalized molecule for use in protein detection. These may or may not include antibodies.

In one embodiment, the antibodies are attached to the surface of the nanoparticles through a molecule known as an alkanethiol. Alkanethiols are a long chain carbon molecules that have a sulfur group on one end and a functional group on the other end. The sulfur end has a high affinity for gold and silver (from which nanoparticles may be produced) which means when a solution of alkanethiols are placed on the nanoparticles, the alkanethiols self-assemble into a monolayer on the surface of the gold. This is known as a self-assembled monolayer (SAM). It results in an ordered layer of molecules with the functional head group sticking up. This functional group can then be used to bind to the protein-specific antibody. A schematic example may be seen in FIG. 7.

Figure 7:
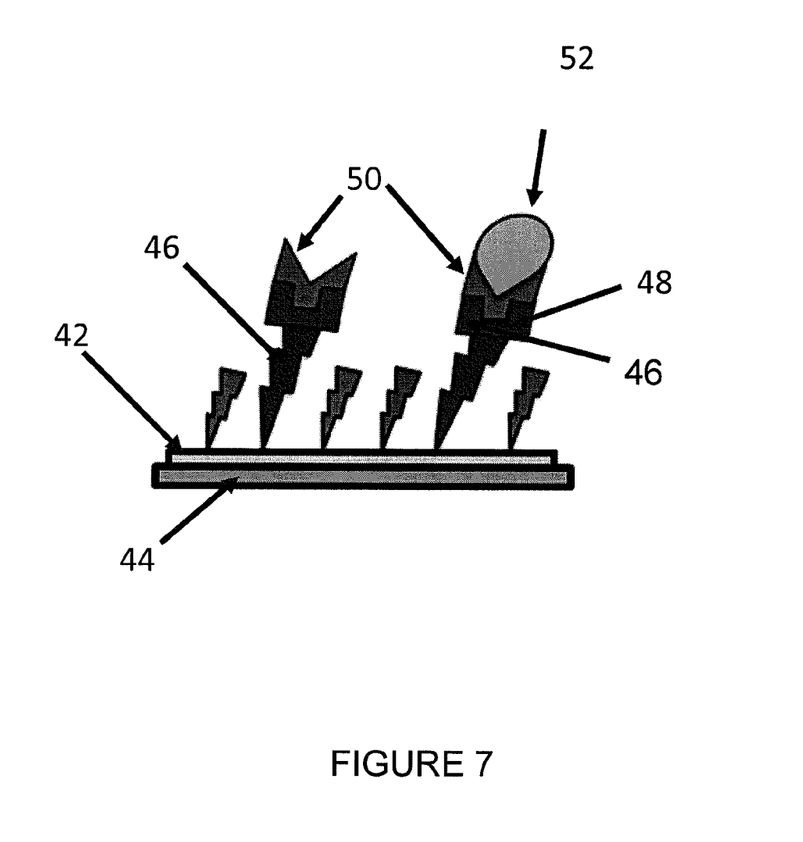
FIG. 7 is a schematic diagram of a protein attached to a functionalized molecule.

A structure of a functionalized surface is shown in FIG. 7. In this example, the nanoparticles 42 are fabricated out of gold and are located on top of a glass ($SiO_2$) substrate 44 or foundation. "Lightning bolts" 46 are alkanethiols that have self-assembled onto the gold surface thereby producing functionalized molecules, or a functionalized surface. The U-shaped portions 48 represent a functional head group that is used to bind to an antibody 50. The protein of interest 52 may then bind specifically to the antibody 50, if it present in the test substance.

In operation, after the functionalized molecules are placed atop the sensor chip, or submerged in the dielectric medium, the light source 16 and the detector 18 may both be turned on or activated. The combination of the LSPR 15 and the RIfS 14 layers provide the ILSPR sensor chip The introduction of a test substance, which may contain a protein of interest, into the dielectric medium, may cause the protein to bind to the antibody, or SAM which causes a change in the local dielectric environment. This shift may be sensed in the light intensity reflected back (or transmitted through, when in transmission mode) to the detector 18. Once the detector 18 senses the reflected (or transmitted) light rays, or intensity, this signal or information is transmitted to the processor 19 which then determines if there has been a change in the refractive index from an expected value, or baseline value.

In one embodiment, where the protein of interest is known, the refractive index of the ILSPR sensor chip 12 with respect to a known functionalized molecule is also known which may be seen as the baseline signal value, and therefore, the processor 19 compares the detected value with this baseline value to determine if there has been a change in the refractive index of the environment surrounding the nanoparticle/RIfS layer or sensor chip 12. In another embodiment, where the sensor unit 10 may be used to determine a plurality of proteins, the expected refractive index or baseline value for each possible protein may be stored in a database, or storage medium, and then retrieved based on user input indicating the protein of interest. In another embodiment, the baseline value may be calculated or determined prior to the introduction of the test substance.

Figure 2A:
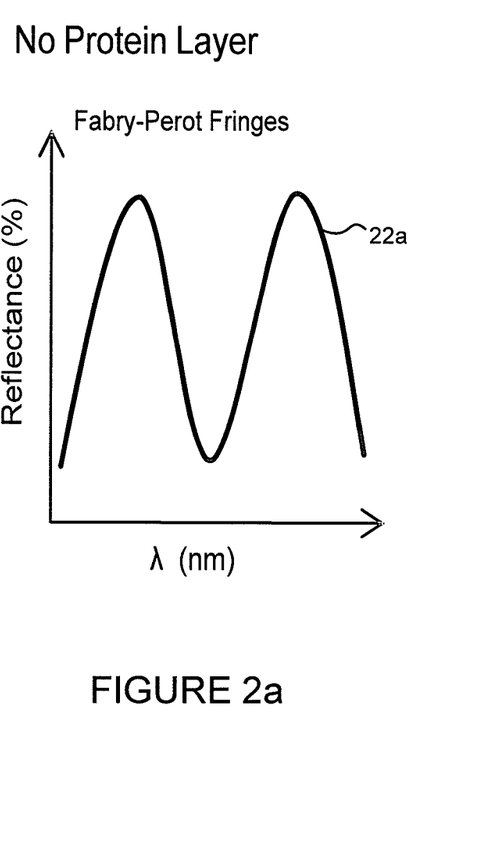
FIG. 2a is a graph showing the percentage reflectance over a span of wavelengths for a dielectric having no protein present.
Figure 2B:
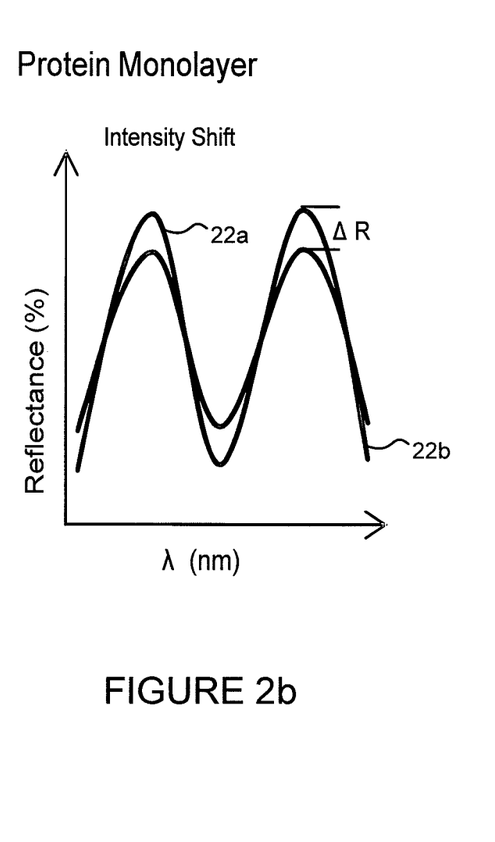
FIG. 2b is a graph showing percentage reflectance over a span of wavelengths for a dielectric medium having a protein introduced.

Turning to FIG. 2a, a graph showing the percentage reflectance over a span of wavelengths for a dielectric medium having no protein present is provided. This may also be seen as the expected value, or baseline value, 22a as discussed above. FIG. 2b is a graph showing percentage reflectance over a span of wavelengths for a dielectric medium having a protein introduced.

As can be seen in FIG. 2b (which also includes the expected values from the graph of 2a), it may be seen that there is a slight intensity shift ($\Delta R$) in the peak values of values retrieved after the test substance 22b is introduced. This difference in the reflectance, or in other words, the change in the refractive index, indicates the presence of the protein and therefore, the processor may then display this message to an individual that the test substance or solution did contain the protein of interest.

In another embodiment, the photodetector obtains a series of readings so that they may be graphed along a curve so that peak values may be compared.

Figure 3:
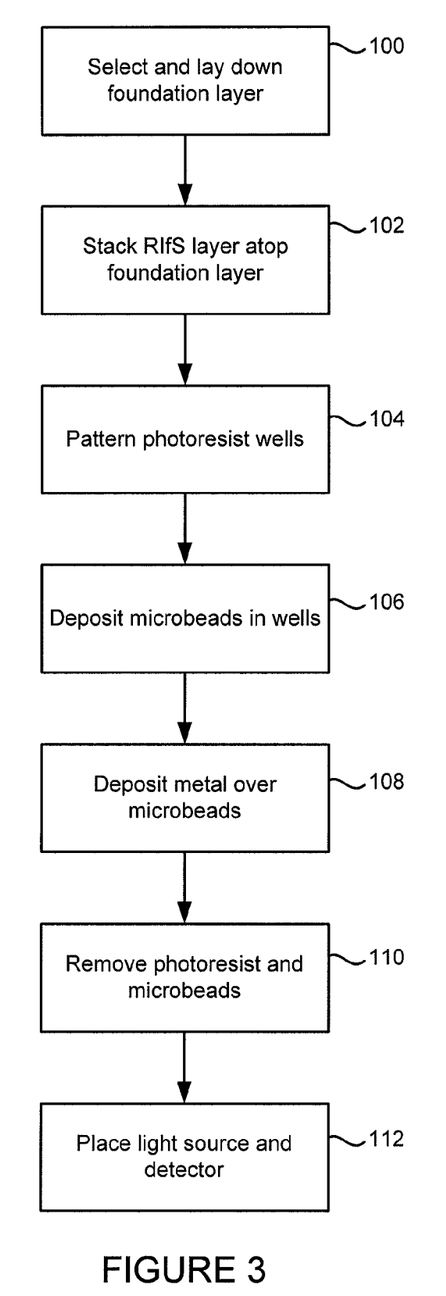
FIG. 3 is a flowchart showing a method for manufacturing an interferometric sensor.

Turning to FIG. 3, a flowchart for manufacturing a sensor unit is shown. FIGS. 4a to 4f are schematic diagrams of various parts of the flowchart of FIG. 3.

Initially, a substrate material is selected and then lain as a foundation layer (100). The foundation layer is manufactured from a transparent material so that the light from the light source may be transmitted towards the nanoparticle array 15. In one embodiment, the substrate material for the foundation layer may be glass, however, other materials, or polymers, such as, but not limited to, polydimethylsiloxane (PDMS) or polycarbonate (PC) may also be used.

After the foundation layer is lain (100), the RIfS sensor layer, is stacked atop the foundation layer (102). The RIfS layer comprises a set of at least two layers made of materials having different refractive indexes. Each layer is stacked atop the other to match the size and shape of the foundation layer and may be stacked in any order. In one embodiment with two layers, the layer made with the material having a lower refractive index is stacked atop the foundation layer and then the layer made with the material having a higher refractive index is stacked atop the lower refractive index material layer (reflectance or reflection mode). In another embodiment, the reverse may be performed with the layer of lower refractive index material stacked atop the layer of higher refractive index material (transmission mode). In the example shown, the material layers have been selected as Tantalum Oxide and Silicon dioxide, however other materials may be selected such as, but not limited to, Zinc Sulfide (ZnS) and Titanium dioxide ($TiO_2$).

Figure 4A:
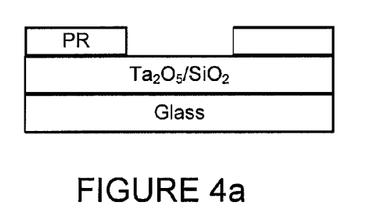
FIGS. 4a to 4g are schematic diagrams of various parts of the flowchart of FIG. 3.
Figure 4B:
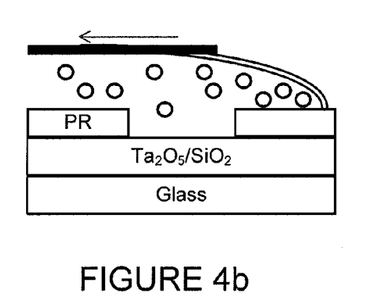
Figure 4C:
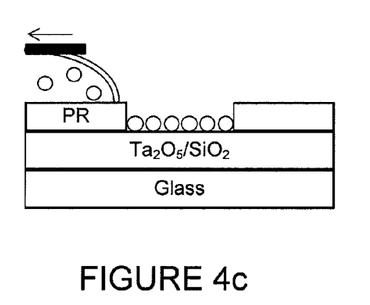

The LSPR sensor layer can be stacked atop of the RIfS layer (103) using different methods (e.g. Nanosphere Lithography (NSL), E-beam lithography, etc.). In a NSL-based method, a layer of photoresist is deposited on top of the last, or uppermost, layer of the RIfS layer and then photoresist wells are patterned (104). In one embodiment, this may be achieved by ultraviolet (UV) photolithography. FIG. 4a provides a schematic diagram of this. After patterning the wells, polymer microbeads, preferably polystyrene in water are deposited into the wells (106) as shown in FIG. 4b. A spreader may be used to assist in the deposition of the microbeads into the wells such as shown in FIG. 4c. The spreader is moved over the surface of the RIfS layer causing the microbeads to self-assemble into closed packed crystals, typically in a hexagonal or cubic pattern.

Figure 4D:
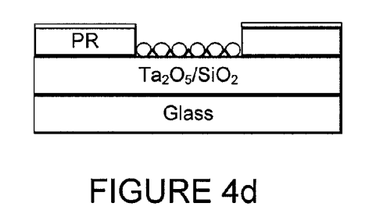

After the beads have been deposited, a thin layer of metal may be deposited (108) over the beads in the well, as schematically shown in FIG. 4d. In a preferred embodiment, the metal is gold or silver, however other materials (e.g. copper) may be contemplated. The deposition of the metal allows the array of nanoparticles to be formed between the interstitial gaps in the closed packed crystals in order to provide the LSPR layer. The size, shape, composition, and orientation of the individual nanoparticles may be controlled via the shape/size of the microbeads. The properties of the nanoparticles behave in different ways depending on their characteristics. Because of the fabrication process, the metal naturally sticks to the surface of the substrate. However, when gold nanoparticles are used and are atop a SiO2, or glass, a very thin layer of chromium is used in between the glass (or $SiO_2$) surface and the gold, which improves adhesion. For silver, typically no chromium layer is needed.

Figure 4E:
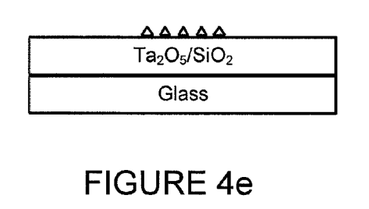
Figure 4F:
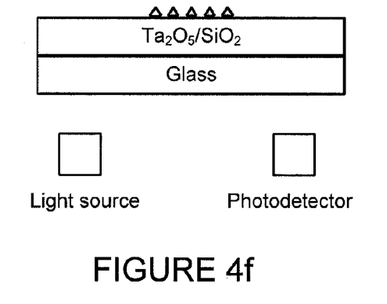

The rest of the photoresist and the microbeads may then be removed (110) leaving only the nanoparticle array atop the RIfS layer, as schematically shown in FIG. 4e. In one embodiment, the photoresist and the microbeads may be removed by a lift-off which is a process creating structures of a target material (the nanoparticles) on the surface of a substrate (the RIfS layer) using a sacrificial material.

Figure 4G:
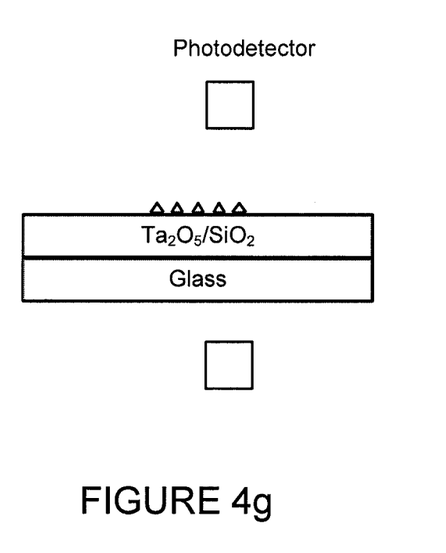

At least one light source and at least one photodetector may be then placed (112) on a side of the RIfS layer away from the nanoparticle array, such that the light source can shine light towards the nanoparticle array and the detector may then sense the light reflected off the nanoparticle array to determine the light intensity so that the processor may determine if a protein of interest is present based on whether the refractive index (or reflectance if in the reflection mode) has changed. In another embodiment (as schematically shown in FIG. 4g), at least one light source and at least one photodetector may be placed on opposite sides of the nanoparticle array so that the photodetector may capture the light transmitted through the nanoparticle array both before and after the test substance is introduced. Calculations may then be obtained from this detection method using light transmission rather than reflection.

Figure 5:
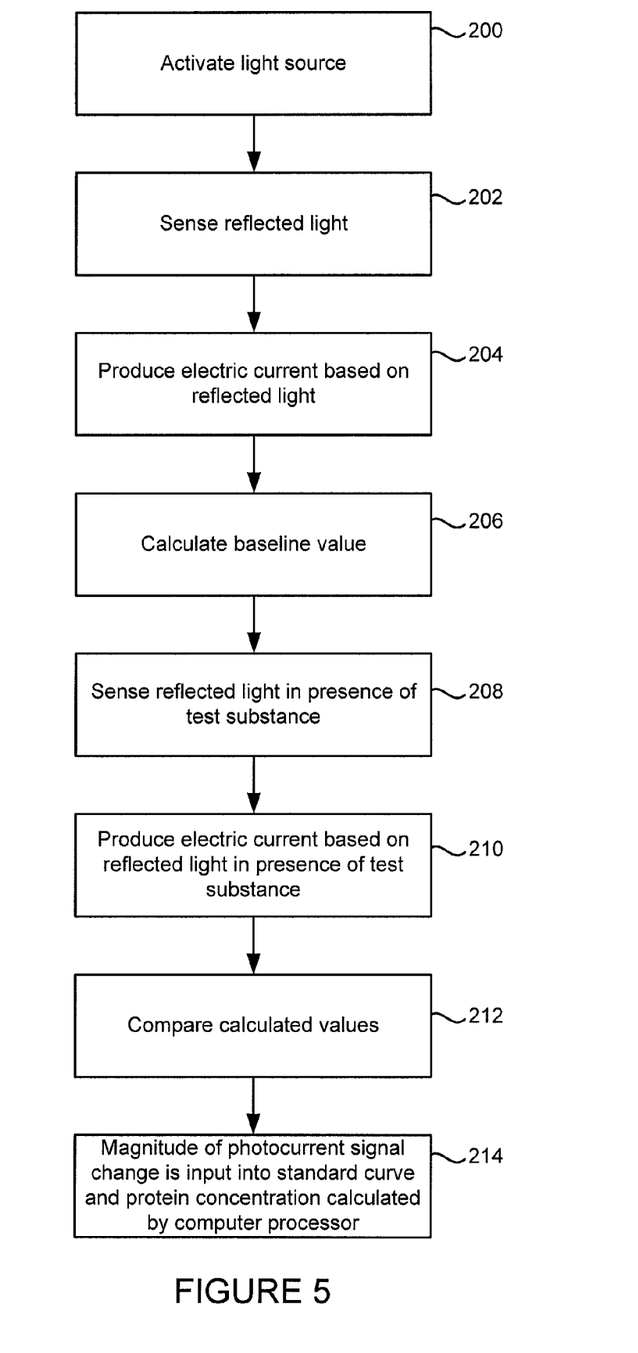
FIG. 5 is a flowchart outlining a data collection process.

Turning to FIG. 5, a flowchart outlining one method of data collection process is shown. After the sensor has been set up for operation in the reflection mode, the light source is activated (200) and light rays are directed at the nanoparticle array or LSPR sensor layer through the interferometric layer. In the reflection mode, the light is then reflected off of the nanoparticle array towards the photodetector which senses the incident light reflected off the sensor chip (202). In the transmission mode, the light is transmitted through the nanoparticle array and then sensed by the photodetector. The photodetector then produces an electric current (204) based on the sensed incident light. This electric current may then be used to calculate a light intensity value, or signal (206). This light intensity value may then be used as the baseline signal. In one embodiment, the baseline signal does not need to be pre-stored but may be regularly determined based on the application for which the sensor is being used. In other words, the sensor may be used for different proteins or chemicals and the baseline signal may be determined on a per use basis so that the sensor may have more varied applications.

After the baseline signal is determined, a test substance, such as a protein sample, may then be injected onto the ILSPR sensor chip in the proximity of the nanoparticle sensor array. Light is then directed (or may be still directed from the original activation) from the light source towards the LSPR nanoparticle sensor array. The reflected light (reflection mode) or transmitted light (transmission mode) in the presence of the test substance is then sensed by the photodetector (208) and once again, an electric current is produced based on the light in the presence of the test substance that is sensed by the photodetector. This may be seen as the test sample value.

This test sample value is then compared to the baseline signal value. If the values are the same, it can be concluded the sample did not include the protein that was being introduced. If the test sample value is less or more than the baseline signal value, it can then be determined that the protein that is being sought is present in the protein sample. If there is a change in value between the test sample value and the baseline signal value, it may be confirmed that the protein or chemical or interest is present.

In other words, if the protein that is introduced into the nanoparticle array binds to the molecules on the nanoparticle array, the refractive index of the environment surrounding the ILSPR sensor chip changes which, in turn, changes the amount of light reflected back to and then sensed by the photodetector.

In another embodiment, multiple light signals may be retrieved for different protein concentrations and then the magnitude of the multiple signals, or photocurrent signal changes, may be graphed or input into a standard curve so the concentration of the protein or chemical of interest may be calculated by a processor. The processor may be integrated with the sensor or this may be done remotely. If the processor is remote, the sensor includes apparatus for transmitting this information to the processor, either via a wired or wireless connection.

In an initial state with a clean LSPR sensor array (devoid of bound antibodies or proteins), some amount of light is being both reflected and transmitted. During functionalization, the addition of an antibody layer to the nanoparticles causes a change in the amount of light being both reflected and transmitted, because the refractive index of the functionalized nanoparticle layer is changed. The antibody is used to allow specific capture of the protein of interest, so the baseline signal is the intensity reading in the presence of the antibody, as during a sensing event, there is no interest in the amount of antibody bound to the LSPR nanoparticle array. The addition of the protein of interest, again, causes a shift in the reflected or transmitted light, and it is the difference between this intensity reading and the baseline that is used to determine the protein concentration.

In one embodiment, the standard curve used for the concentration calculation may be represented by the following linear equation $C_{protein}=(\Delta I * s)$ whereby $C_{protein}$ is the concentration of protein (ng/ml), $\Delta I=I_1-I_2$ is the change in photocurrent (A) measured before protein absorption ($I_1$) and after protein absorption ($I_2$), and "s" is the sensitivity of the sensor, in ng/ml/A, which has been previously determined experimentally for the protein of interest.

As discussed above, the sensor has a characteristic sensitivity value, "s", which represents an amount of protein (ng/ml) required to produce a change in photocurrent of 1 A. This value may be experimentally determined for the protein of interest, by taking samples of protein in which the concentration is known, injecting these samples separately into the sensor, and measuring the photocurrent signal change for each different known concentration. By plotting the photocurrent signal change vs. protein concentration, the sensitivity can be easily determined from the slope of the line of best fit through the data points.

As different proteins have different sensitivity values, if the sensing unit is designed to only detect one protein of interest, only the sensitivity value for the specific protein is needed.

As will be understood, this is just one example of an equation for this calculation. Other more complex equations may be used, as the exact relation between concentration and photocurrent may not be linear.

In one embodiment, each sensing unit or sensor chip is designed for use with one specific protein, as the surface of the interferometric layer and the nanoparticle array may be engineered to only interact with a specific protein of interest. In another embodiment, the functionalized LSPR sensor layer of the ILSPR sensor chip may be regenerated so that it can be used more than once. The ILSPR sensor chip may be regenerated by the user while it is still in the sensing unit (i.e. in situ), or it may regenerated in an external lab.

Figure 8:
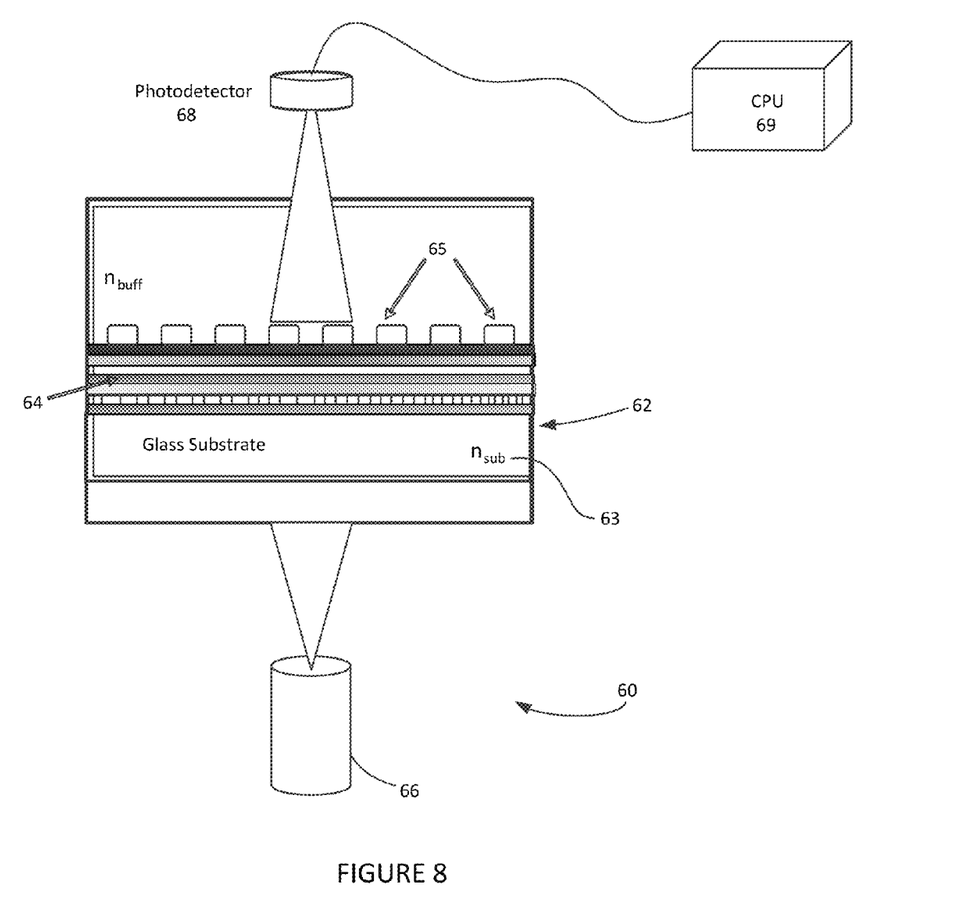
FIG. 8 is a schematic diagram of an interferometric sensing unit for use in a transmission mode.

In an alternative embodiment (as shown in FIG. 8), a sensing unit 60 for use in a transmission mode is shown. The sensing unit 60 includes a sensor chip 62. Similar to the sensing unit of FIG. 1, the sensing unit includes a photodetector 68 which may be located away from light source 66 and may sense the light that passes through the nanoparticle array 65 and the interferometric layer 64. As shown, the interferometric layer 64 includes a plurality of layers of refractive material atop the foundation layer 63. As discussed above, the interferometric layer may include any number of refractive material layers. The photodetector 68 is in communication with a CPU 69. Operation of this embodiment is similar to the one described above with respect to the reflection mode with the location of the photodetector being one difference. For this embodiment, the photodetector would be located on a side of the LSPR nanoparticle array opposite the light source. In other words, the interferometric sensor calculates the values based on the transmission of light rather than the reflection of light.

In an alternative embodiment, the ILSPR sensor chip is designed for sensing the presence of a chemical of interest, based on light which is reflected back to or transmitted direct to a photodetector when the test substance is introduced. In this embodiment, the ILSPR sensor chip would operate in the same way as when used as a protein sensor. However, instead of using functionalized molecules (i.e., self-assembled monolayers and antibodies), a different type of layer would be used to capture the specific chemical of interest. This could be, for example, a polymer layer on top of the nanoparticles, which has a high affinity for a certain chemical. Absorption of the chemical into the polymer would change the refractive index of the nanoparticle layer or LSPR sensor layer thereby changing the light intensity and photocurrent detected. The magnitude of the change would depend on the chemical concentration, and sensitivity values could be determined (similarly to what was described above) for each chemical of interest.

Figure 6:
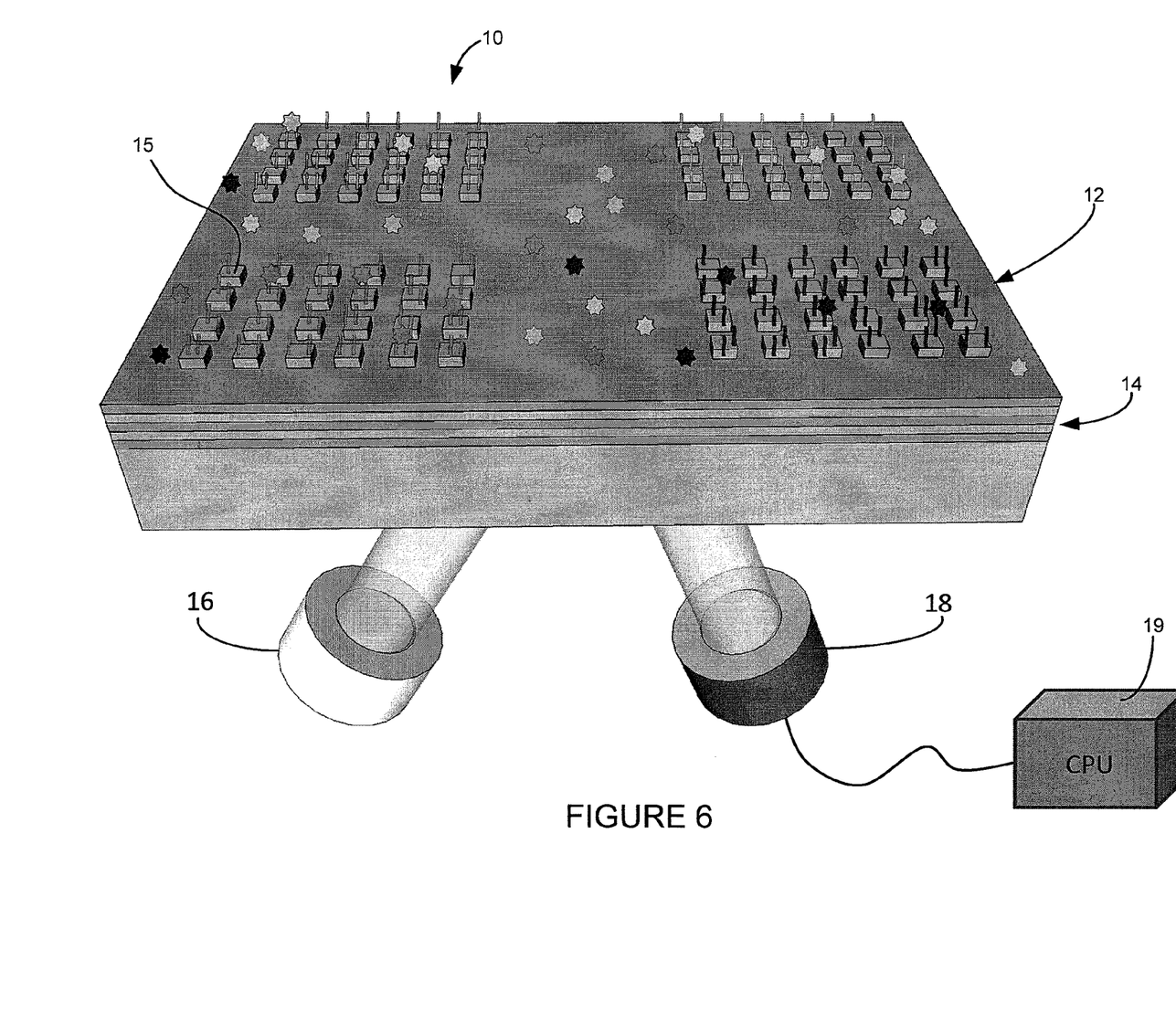
FIG. 6 is a schematic diagram of a multiplexed sensor system.

Turning to FIG. 6, a perspective view of a multiplexed sensor in reflection mode is shown. Similarly to the single protein or chemical sensor, if the sensor is used in a transmission mode, the photodetector would be located adjacent to the LSPR nanoparticle sensor layer. For a multiplexed device, the most likely format would be a single light source and four separate photodiodes as the set of photodetectors. However, it is also possible to use a single photodetector if a charge coupled device (CCD) is used as the photodetector instead of a photodiode. In the case of the CCD, the pixels may be split into different regions, with one region for each different protein of interest being detected. The light intensity from each region can be determined independently, removing the need for four separate detectors. In this embodiment, the most viable option for the light source would be a white light emitting diode to produce a high intensity and stable source of light.

The above-described embodiments are intended to be examples only. Alterations, modifications and variations can be effected to the particular embodiments by those of skill in the art without departing from the scope, which is defined solely by the claims appended hereto.

What is claimed is:

1. An interferometric localized surface plasmon resonance sensor (ILSPR) unit comprising:
   an ILSPR sensor chip, the sensor chip including a localized surface plasmon resonance sensor (LSPR) layer, an interferometric sensing layer, and a transparent surface material;
   at least one light source for directing light through the ILSPR sensor chip at the LSPR layer; and
   a photodetector for sensing a level of light intensity after the light has struck the LSPR layer;
   wherein the interferometric sensing layer is a narrowband filter.

2. The ILSPR unit of claim 1 wherein the photodetector is on a same side of the sensor chip as the light source.

3. The ILSPR unit of claim 1 wherein the photodetector is on the same side of the sensor chip as the LSPR layer.

4. The ILSPR unit of claim 1 wherein the LSPR layer is an array of nanoparticles.

5. The ILSPR unit of claim 4 wherein individual nanoparticles within the array of nanoparticles are functionalized with self-assembled monolayers (SAMs).

6. The ILSPR unit of claim 5 wherein the SAMs are of alkanethiol based molecules.

7. The ILSPR unit of claim 1 wherein the interferometric sensing layer comprises at least two of layers of refractive material.

8. The ILSPR unit of claim 1 wherein the interferometric sensing layer is a reflectrometric interference spectroscopy (RIfS) layer.

9. The ILSPR unit of claim 1 wherein the interferometric sensing layer comprises:
   a layer of high refractive index material; and
   a layer of low refractive index material.

10. The ILSPR unit of claim 9 wherein the layer of high refractive index material and the layer of low refractive index material are stacked.

11. The ILSPR unit of claim 10 wherein the layer of high refractive index material is closer to the LSPR layer than the layer of low refractive index material.

12. The ILSPR unit of claim 10 wherein the layer of low refractive index material is closer to the LSPR layer than the layer of high refractive index material.

13. The ILSPR unit of claim 1 wherein the LSPR layer is located within a dielectric medium.

14. The ILSPR unit of claim 1 wherein the LSPR layer is within a dielectric medium.

15. The ILSPR unit of claim 14 wherein the dielectric medium is Phosphate Buffered Saline (PBS).

16. The ILSPR unit of claim 1 wherein the narrowband filter comprises cutoffs designed to be on or near a LSPR peak wavelength.

17. A method of manufacturing an interferometric localized surface plasmon resonance sensor (ILSPR) unit comprising:
    obtaining a transparent foundation substrate layer;
    stacking an interferometric sensing layer atop the transparent foundation substrate layer, the interferometric sensing layer acting as a narrowband filter;
    mounting a localized surface plasmon resonance sensor (LSPR) layer atop the interferometric sensing layer; and
    pouring or flowing a dielectric medium atop the interferometric sensing layer which submerges the LSPR layer.

18. The method of claim 17 further comprising:
    placing at least one light source on a side of the transparent foundation substrate layer away from the interferometric sensing layer so that the transparent foundation substrate layer is closer to the at least one light source than the interferometric sensing layer is to the at least one light source.

19. The method of claim 18 further comprising:
    placing a photodetector or a CCD camera adjacent to the at least one light source.

20. The method of claim 18 further comprising:
    placing a photodetector or a CCD camera apart from the at least one light source.

21. The method of claim 17 wherein stacking the interferometric sensing layer comprises:
    stacking a layer of high refractive index material atop the transparent foundation substrate layer; and
    stacking a layer of low refractive index material atop the layer of high refractive index material.

22. The method of claim 17 wherein stacking the interferometric sensing layer comprises:
    stacking a layer of low refractive index material atop the transparent foundation substrate layer; and
    stacking a layer of high refractive index material atop the layer of low refractive index material.

* * * * *